US00PP31637P3

(12) United States Plant Patent
Hillier

(10) Patent No.: US PP31,637 P3
(45) Date of Patent: Apr. 7, 2020

(54) ***CORYDALIS* PLANT NAMED 'PORCELAIN BLUE'**

(50) Latin Name: *Corydalis flexuosa*
Varietal Denomination: Porcelain Blue

(71) Applicant: John G. Hillier, Hampshire (GB)

(72) Inventor: John G. Hillier, Hampshire (GB)

( * ) Notice: Subject to any disclaimer, the term of this patent is extended or adjusted under 35 U.S.C. 154(b) by 0 days.

(21) Appl. No.: 16/350,845

(22) Filed: Jan. 23, 2019

(65) Prior Publication Data

US 2019/0246545 P1 Aug. 8, 2019

(30) Foreign Application Priority Data

Feb. 6, 2018 (QZ) ..... PBR 2018/0427

(51) Int. Cl.
*A01H 5/02* (2018.01)
*A01H 6/00* (2018.01)

(52) U.S. Cl.
USPC ..... Plt./263.1
CPC ..... *A01H 6/00* (2018.05); *A01H 5/02* (2013.01)

(58) Field of Classification Search
USPC ..... Plt./263.1
CPC ..... A01H 6/00; A01H 5/02
See application file for complete search history.

*Primary Examiner* — Keith O. Robinson
(74) *Attorney, Agent, or Firm* — Barbara Campbell; James M. Weatherly; Cochran Freund & Young LLC

(57) ABSTRACT

A new cultivar of *Corydalis* named 'Porcelain Blue' that is distinguishable by its compact upright plant habit, profuse basal branching, deeply cut leaves with multiple lobes, and flowers which are vibrant aquamarine blue in color and which flower over a long period including summer.

2 Drawing Sheets

Genus and species: *Corydalis flexuosa.*
Variety denomination: 'Porcelain Blue'.

CROSS REFERENCE TO RELATED APPLICATIONS

This application claims the benefit of priority under 35 U.S.C. 119 (f) to the application for European Community Plant Variety Rights which was filed for the instant plant variety on Feb. 6, 2018, File Number 2018/0427.

BACKGROUND OF THE NEW PLANT

The present disclosure relates to a new and distinct cultivar of *Corydalis* plant, also known as a Blue *Corydalis*, a perennial plant that is grown for use as an ornamental landscape and container plant. The new variety will be referred to hereinafter by the cultivar name 'Porcelain Blue'.

'Porcelain Blue' originated and was selected by the inventor as a single plant which the inventor had observed at the inventor's nursery in Romsey, Hampshire, United Kingdom. For many years prior to 2005, the inventor's nursery maintained a collection of named and unnamed plants (all unpatented) of the species *Corydalis flexuosa*. New plants were raised from seed collected from plants within the collection which had set seed as a result of exposure to open pollination. In 2005, the inventor observed that one plant, subsequently named 'Porcelain Blue' exhibited a denser and stiffer habit relative to plants which are typical of the species parent and relative to plants which are generally raised from seed of the species parent. The inventor observed that 'Porcelain Blue' bore grey-green leaves which are more deeply cut than leaves of the species. The inventor has maintained the original plant of 'Porcelain Blue' since 2005 and has observed in particular that 'Porcelain Blue' has a very long flowering period, including the summer months when the species itself tends to become dormant and out-of-flower.

'Porcelain Blue' was first asexually propagated in 2010 using the method of division in a greenhouse at the inventors nursery in Romsey, Hampshire, United Kingdom. The inventor has confirmed that 'Porcelain Blue' is stable and reproduces true to type in successive generations of asexual reproduction.

SUMMARY

The following traits have been repeatedly observed and represent the distinguishing characteristics of 'Porcelain Blue'. 'Porcelain Blue' has not been tested under all possible conditions and phenotypic differences may be observed with variations in environmental, climatic, and cultural conditions, without however, any variance in genotype.

1. 'Porcelain Blue' exhibits a compact broad plant habit.
2. After 18 months' growth in a one gallon container, 'Porcelain Blue' achieves height and breadth of 35 cm.
3. 'Porcelain Blue' exhibits profuse basal branching.
4. The foliage color of 'Porcelain Blue' is grey-green in color.
5. The leaves of 'Porcelain Blue' are deeply cut with multiple lobes.
6. The flowers of 'Porcelain Blue' are vibrant aquamarine blue in color.
7. 'Porcelain Blue' flowers over a long period.
8. 'Porcelain Blue' does not exhibit summer flowering dormancy.

BRIEF DESCRIPTION OF THE PHOTOGRAPHS

The accompanying color photographs illustrate the overall appearance of 'Porcelain Blue' showing the colors as true as it is reasonably possible to obtain in colored reproductions of this type. Colors in the drawing may differ from the color values cited in the detailed botanical description, which accurately describe the actual colors of the new variety 'Porcelain Blue'.

Figure 1:
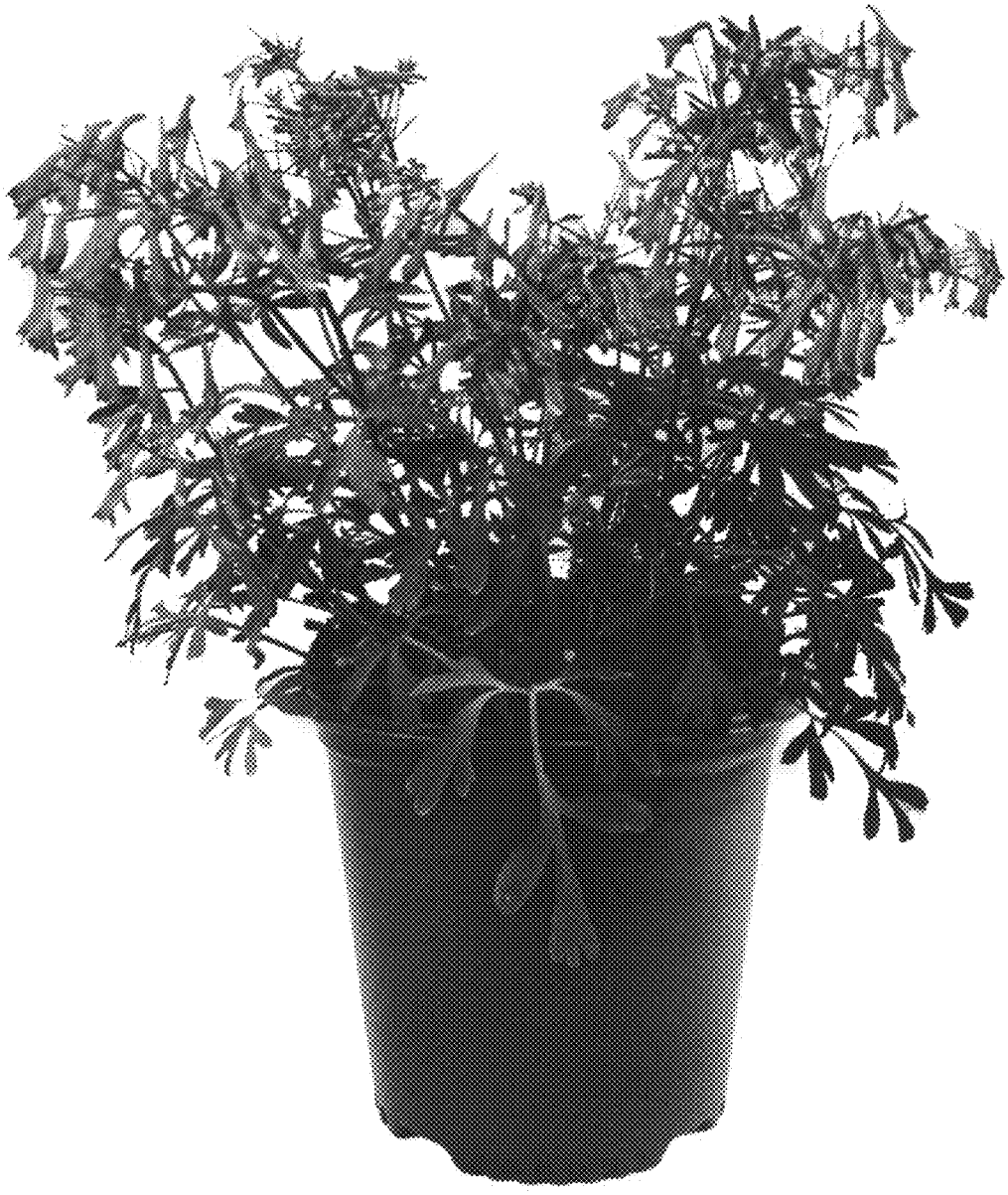
FIG. 1 shows a mature plant of 'Porcelain Blue'.
Figure 2:
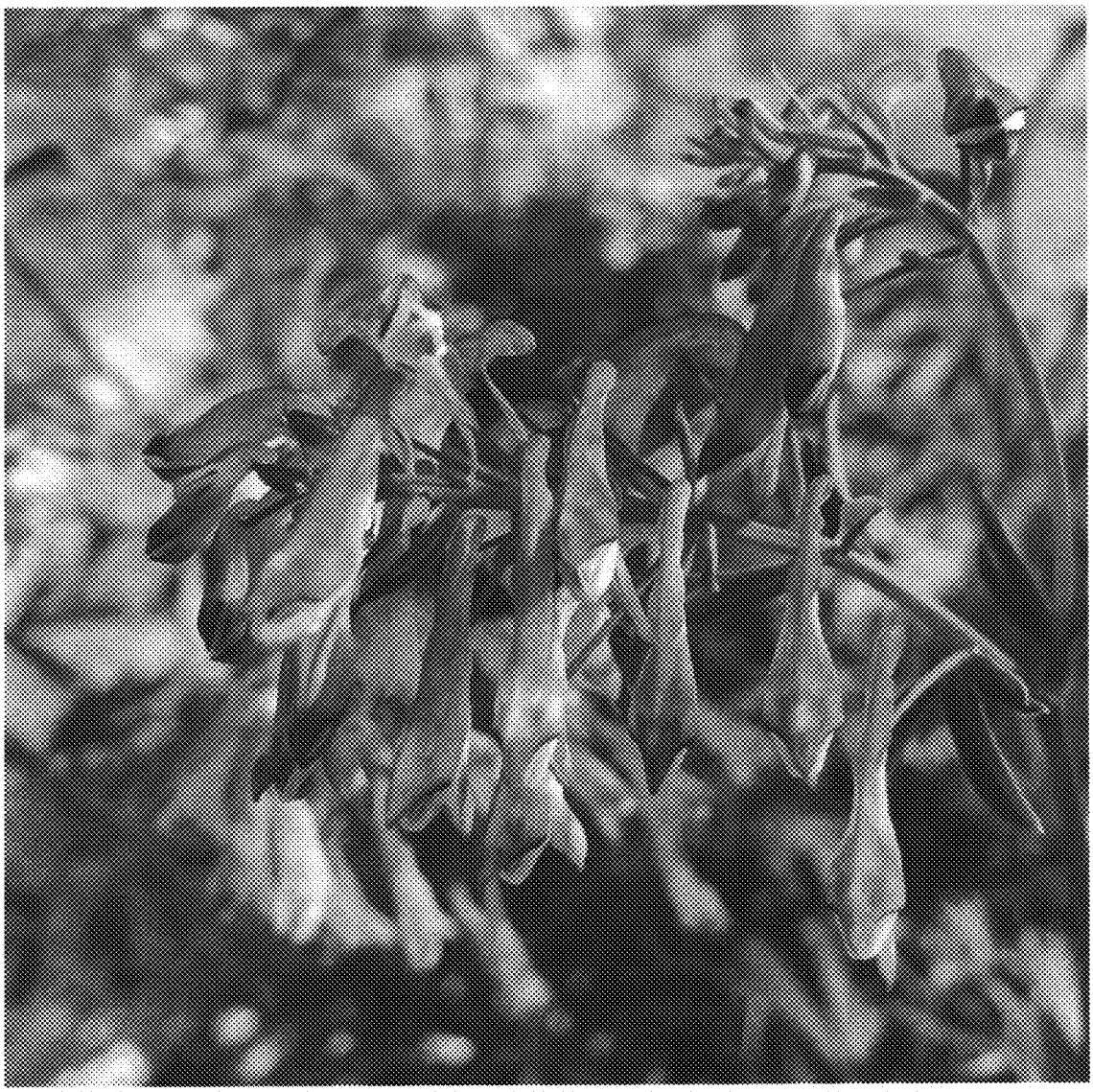
FIG. 2 shows a close-up view of the inflorescence of 'Porcelain Blue'.

Photographs were taken in April 2017 in Santa Barbara, Calif. using an 18 months old plant (from a single division) grown out of doors in full sun.

BOTANICAL DESCRIPTION OF THE PLANT

The following detailed descriptions set forth the distinctive characteristics of 'Porcelain Blue'. Observations, measurements, values, and comparisons were collected between April 2018 and January 2019 in Santa Barbara, Calif. from an 18 to 24 months old plant which was growing outdoors in full sun in a 1 gallon container. The plant had been grown naturally, without any pinching or use of chemical growth regulator. Color determinations were made in accordance with The 2007 Royal Horticultural Society Colour Chart from London England, except where general color terms of ordinary dictionary significance are used.

Classification:
- *Family*.—Fumariaceae.
- *Genus*.—*Corydalis*.
- *Species*.—*flexuosa*.
- *Common name*.—Blue *Corydalis*.

Parentage: Seedling raised from the species *Corydalis flexuosa* (unnamed, unpatented).

Plant:
- *Propagation method*.—Division, tissue culture.
- *Rooting system*.—Rhizomatous. Rhizomes horizontal, short and scaly giving rise to fine fibrous roots. Rhizome color ranges between N199C and 202A.
- *Vigor*.—Vigorous basal branching.
- *Time to develop roots*.—Approximately 3 weeks are required for a newly planted division to become established on its own rhizome and roots.
- *Crop time*.—Approximately 14 to 16 weeks are required to produce a flowering plant in a 1 gallon container from a rooted division or liner.
- *Suggested container size*.—1 gallon container and larger if desired.
- *Use*.—Ornamental for use as a landscape plant or container plant.
- *Type*.—Perennial.
- *Overall dimensions*.—After one year's growth in a 1 gallon: 35 cm in height (including the inflorescence), 35 cm in width.
- *Cultural requirements*.—Grow in full sun with moderate water and well-draining soil.
- *Hardiness*.—USDA Zone 5.
- *Growth habit*.—Compact, broad habit, flower stems gently arching.
- *Blooming season*.—At least from spring until fall. 'Porcelain Blue' does not exhibit summer flowering dormancy and has been observed to flower in mild climates all year round.
- *Lastingness of blooms*.—Each inflorescence has some flower for 14 days, individual flowers last for 5 to 7 days.

Stems (measured from soil emergence to base of inflorescence):
- *Length*.—25 cm.
- *Diameter*.—3 mm.
- *Color*.—Ranges between 174B and N186A.
- *Shape*.—Rounded tetragonal.
- *Texture*.—Glabrous.
- *Strength*.—Stiff, wiry. Stems will arch under the weight of full inflorescence.
- *Lateral stems*.—Rarely present. Where present, lateral stems arise very low down, at or slightly above soil surface.
  - *Length*.—25 cm.
  - *Diameter*.—3 mm.
  - *Color*.—Ranges between 174B and N186A.
  - *Shape*.—Rounded tetragonal.

Leaves:
- *Type, arrangement*.—Compound, biternate, alternate.
- *Attachment*.—Petiolate (short petioles) except for leaflets on lateral stems, sessile.
- *Quantity per stem*.—3 to 5.
- *Shape*.—Deltoid overall.
- *Division*.—Deeply irregularly divided, typically into 3 primary lobes which are further divided into three secondary lobes.
- *Length* (*leaf overall*).—5 cm to 8 cm.
- *Width* (*leaf overall*).—3 cm to 5 cm.
- *Length* (*each lobe, typical*).—Primary lobes 3 cm, secondary lobes 2 cm.
- *Width* (*each lobe, typical*).—Primary lobes 2 cm, secondary lobes 1 cm.
- *Thickness*.—0.5 mm to 1.0 mm, slightly fleshy.
- *Venation*.—Palmate.
- *Texture* (*both surfaces*).—Glaucous.
- *Color* (*both surfaces*).—Ranges between N138C and 189A.
- *Margin*.—Entire.
- *Apex*.—Obtuse.
- *Base*.—Cuneate.

Petiole:
- *Shape*.—Round.
- *Length*.—1 cm to 4 cm.
- *Width*.—2 mm.
- *Texture*.—Glabrous.
- *Color*.—189A.

Peduncle:
- *Length*.—8 cm.
- *Diameter*.—3 mm.
- *Shape*.—Rounded tetragonal.
- *Texture*.—Glaucous.
- *Color*.—178A, becoming N170B to 172B towards and within the inflorescence.

Inflorescence:
- *Type*.—Raceme
- *Dimensions*.—8 cm to 10 cm in overall length, 4 cm to 5 cm in overall diameter.
- *Number of flowers per raceme*.—16 to 20.
- *Bloom period*.—At least from April to October. Year-round flowering has been observed in warm winter climates.
- *Lastingness of color in inflorescence*.—14 days.

Pedicel:
- *Length*.—8 cm.
- *Diameter*.—3 mm.
- *Shape*.—Round.

*Texture*.—Glaucous.

*Color*.—172B.

Flowers:

*Type*.—Zygomorphic.

*Buds*.—Length (before opening): 1.5 cm. Diameter (before opening): 0.75 cm. Shape: Tubular, obovate. Color: Emerges 147C, developing blue 107B on upper surface.

*Flowers*.—Corolla: Consists of fused pairs of upper and lower petals. All petals fuse to form spur at base. Corolla tube length: 3.5 cm. Corolla tube diameter: 1 cm. Shape: Tubular. Color: Outwardly 107B; opens to expose inner surfaces of upper and lower petals, 101D to NN155C.

*Lastingness of flower*.—5 to 7 days.

*Fragrance*.—Sweet, honeyed.

Sepals: Not observed, absent.

Petals:

*Upper petals*.—Quantity: 2, fused longitudinally except free apex. Upper petals form a 2 mm high crest towards, but not reaching, the apex. Dimensions (both petals as fused): 3.5 cm in length, 0.8 cm in width at widest section. Color (outside surface): Predominantly 107B, with occasional patches of very pale blue to white (108D to NN155C) towards apex and on crest. Apex color commences N92A as flower opens, becoming 107B as upper and lower petals separate. Color (inside surface): 101D to NN155C. Texture: Glabrous (both surfaces), lustrous (outer surface). Apex: Free (unfused), shape acute. Apex margin color, N92A. Base (spur): Rounded. Spur shape: Narrowly cylindrical, curved downwards. Spur dimensions: 4 mm in length, 1.5 mm in diameter. Spur color: 107B. Spur texture: Glabrous.

*Lower petals*.—Quantity: 2, fused longitudinally, terminating in small claw at apex. Dimensions (both petals as fused): 3.5 cm in length, 0.8 cm in width. Color (outside surface): 101D becoming darker 107B towards apex and base. Color (inside surface): 101D and white NN155C. Texture (both surfaces): Glabrous. Apex: Mucronate, recurved claw-like. Apex margin color, N92A. Base: Rounded.

Reproductive organs:

*Stamens*.—Two, 15 mm in length, consisting of close bundle of 3 translucent filaments, color N155C.

*Anthers*.—Small, globular, 2 mm in diameter, color 155B.

*Pollen*.—Absent.

*Pistil*.—One, 8 mm in length.

*Stigma*.—Flattened quadrangular with 4 globular appendages, approximately 1 mm in diameter, color 1D.

*Style*.—4 mm in length, obscured by 4 to 6 papillae closely adjacent to style. Papillae white NN155C with dark grey-black (between 202B and 202A) longitudinal streaks.

*Ovary*.—Not observed.

Seed: Not observed in repeated observations.

Disease and pest resistance or susceptibility: None observed.

COMPARISON WITH PARENTAL LINES AND KNOWN VARIETY

'Porcelain Blue' is distinguishable from the species parent *Corydalis flexuosa* as follows. Whereas plants typically raised from seed of the species grow with a loose, open habit and flower only or mainly in the spring, 'Porcelain Blue' exhibits vigorous basal branching and a very long flowering season, including summer.

'Porcelain Blue' may be compared with many varieties of *Corydalis flexuosa* which are known to the inventor, including 'Purple Leaf' (unpatented), 'Pere David' (unpatented), 'China Blue' (unpatented) and 'Blue Panda' (unpatented). All of these varieties exhibit summer flowering dormancy whereas 'Porcelain Blue' flowers continuously through the summer months. In addition, the variety 'Purple Leaf' bears purple-tinged foliage and pink-tinged flowers, and the variety 'Pere David' exhibits a broadly spreading plant habit.

'Porcelain Blue' may also be compared with *Corydalis* Plant Named 'COURIBLUE' (U.S. Plant Pat. No. 25,277). Whereas both varieties 'Porcelain Blue' and 'COURIBLUE' bear blue flowers, the foliage of 'Porcelain Blue' is distinguishable by its grey-green color and by its deeply cut compound leaves. In addition, the growth habit and the presentation of the flowers of 'COURIBLUE' is upright whereas 'Porcelain Blue' exhibits a broader plant habit and gently arching flower stems.

I claim:

1. A new and distinct cultivar of *Corydalis* plant named 'Porcelain Blue' as described and illustrated herein.

* * * * *